(12) United States Patent  (10) Patent No.: US 7,587,076 B2
Kraus et al.  (45) Date of Patent: Sep. 8, 2009

(54) FLUOROSCOPY IMAGE VERIFICATION

(75) Inventors: Florian Kraus, Haar (DE); Christian Maier, München (DE)

(73) Assignee: BrainLAB AG, Feldkirchen (DE)

( * ) Notice: Subject to any disclaimer, the term of this patent is extended or adjusted under 35 U.S.C. 154(b) by 797 days.

(21) Appl. No.: 11/217,062

(22) Filed: Aug. 31, 2005

(65) Prior Publication Data

US 2006/0050988 A1   Mar. 9, 2006

Related U.S. Application Data

(60) Provisional application No. 60/655,596, filed on Feb. 23, 2005.

(30) Foreign Application Priority Data

Aug. 31, 2004   (EP)   ................................. 04020625

(51) Int. Cl.
*G06K 9/00* (2006.01)
*A61B 6/02* (2006.01)
(52) U.S. Cl. ......................................... 382/128; 378/42
(58) Field of Classification Search ................ 382/128, 382/129, 130, 131, 132, 133, 134, 151, 294; 378/6, 42, 44, 190, 46, 63, 140; 600/407, 600/410, 416, 425, 310, 436, 473; 601/41; 701/27, 40, 44, 77, 98, 200, 206; 128/920, 128/922
See application file for complete search history.

(56) References Cited

U.S. PATENT DOCUMENTS

| | | | |
|---|---|---|---|
| 5,951,475 A * | 9/1999 | Gueziec et al. ............. 600/425 |
| 6,336,899 B1 * | 1/2002 | Yamazaki .................... 600/443 |
| 6,481,888 B1 * | 11/2002 | Morgan ....................... 378/204 |
| 6,662,036 B2 * | 12/2003 | Cosman ....................... 600/411 |
| 6,697,664 B2 * | 2/2004 | Kienzle, III et al. ......... 600/427 |
| 7,194,295 B2 * | 3/2007 | Vilsmeier ..................... 600/416 |
| 2004/0015176 A1 | 1/2004 | Cosman | |
| 2004/0097805 A1 * | 5/2004 | Verard et al. ................ 600/428 |

OTHER PUBLICATIONS

European Search Report for corresponding Application No. 04020625 dated Jan. 27, 2005.

* cited by examiner

*Primary Examiner*—Abolfazl Tabatabai
(74) *Attorney, Agent, or Firm*—Renner, Otto, Boisselle & Sklar, LLP

(57) ABSTRACT

A system and method for verifying the registration of a fluoroscopy image, wherein an artificial landmark array is introduced into a radiation path of a fluoroscopy apparatus, the landmark array being trackable by a computer assisted, medical navigation system. A fluoroscopy recording is produced with the aid of the fluoroscopy apparatus, and a spatial position of the artificial landmark array at the time the fluoroscopy recording is produced is detected and stored. The fluoroscopy recording is registered onto previously acquired body image data of the navigation system using marking points mapped on the fluoroscopy recording, wherein the marking points are maps of markings on the radiation source. Verification is based on a correspondence between an image shadow of the artificial landmark array on the fluoroscopy recording and a position of the landmark array at the time the recording was produced.

18 Claims, 2 Drawing Sheets

FLUOROSCOPY IMAGE VERIFICATION

RELATED APPLICATION DATA

This application claims priority of U.S. Provisional Application No. 60/655,596 filed on Feb. 23, 2005, which is incorporated herein by reference in its entirety.

FIELD OF THE INVENTION

The present invention relates generally to registration of a fluoroscopy image. More particularly, the invention relates to verification of the acquisition accuracy for a fluoroscopy image that is registered within fluoroscopy-based navigation software.

BACKGROUND OF THE INVENTION

Fluoroscopy images, for example, can be acquired with the aid of a C-arc fluoroscopy apparatus. The images then can be transferred to a navigation system, which uses the images as a basis for image-assisted or image-guided surgery. One precondition for accurate image-assisted or image-guided surgery is establishing a spatial correlation between a virtual representation of a patient or body data and an actual anatomy of the patient. This process is called registration. The present invention allows the accuracy of this registration process for fluoroscopy images to be verified.

Verification is beneficial because errors, which are undesirable, can occur in the registration process. Verification detects these errors and, thus, provides an indication of being within a specified or desired tolerance. Registration is often achieved by mapping points or markings on the fluoroscopy images, said markings being arranged in a known position on an attachment of the C-arc radiation source. If, however, an insufficient number of markers are mapped, or the mapping is inaccurate, registration errors can result.

U.S. Pat. Nos. 6,697,664, 6,675,040 and 6,662,036 include descriptions of the principle of fluoroscopic navigation. However, these references do not provide solutions for reducing or minimizing registration errors.

SUMMARY OF THE INVENTION

The invention relates to a system and method for verifying the registration of a fluoroscopy image. In accordance with the invention, an image shadow of an artificial landmark on a fluoroscopy recording and a position of an actual landmark at the time the recording was produced are compared. If the comparison is within a desired range, the registration is deemed acceptable. Otherwise, a new fluoroscopic image is requested and the process can be repeated.

In one embodiment, there is provided a method for verifying the registration of a fluoroscopy image. In accordance with the method, an artificial landmark array is introduced into a radiation path of a fluoroscopy apparatus, the landmark array being trackable by a computer assisted, medical navigation system. A fluoroscopy recording is produced with the aid of the fluoroscopy apparatus, and a spatial position of the artificial landmark array at the time the fluoroscopy recording is produced is detected and stored. The fluoroscopy recording is registered onto previously acquired body image data of the navigation system using marking points mapped on the fluoroscopy recording, wherein the marking points are maps of markings on the radiation source. A correspondence between an image shadow of the artificial landmark array on the fluoroscopy recording and a position of the landmark array at the time the recording was produced is checked and, if within a desired range or tolerance, the registration is deemed acceptable. The correspondence can be checked via an output unit of the navigation system.

Checking the correspondence between the artificial landmark array image shadow and the position reproduced in the navigation system enables the registration accuracy to be verified, irrespective of the patient registration and tracking equipment used. As a result, it is not necessary, within the framework of the invention, for the position of the landmark array to remain fixed or constant. Accordingly, fixing the landmark array with the aid of complicated equipment (which may be an obstruction during an operation) can be avoided. Further, since the spatial position of the landmark array can be stored, the invention enables removal or displacement of the array once the image(s) have been produced. This makes it possible, for example, to simply place the artificial landmark array on the patient while the verification recording is produced. Displacement of the patient's skin or of the landmark array (e.g., the patient is covered resulting in the array being displaced) does not have a negative effect on verification. Accordingly, it is not necessary to fixedly arrange the landmark array on an exposed bone. Thus, the invention enables a minimally invasive or even non-invasive way of verifying the registration accuracy of a fluoroscopy image.

An additional advantage is that using the artificial landmark array allows a fluoroscopy image to be verified, even when conventional verification or registration using natural landmarks is not possible or would only be possible if further invasive incisions were made. This applies, for example, to registration in soft tissue and on long bones in the intermediate area of the bone, where no useful natural landmarks can be acquired.

If an insufficient correspondence is established, it is possible to request or prompt a new fluoroscopy recording to be produced. As noted above, it is advantageous within the framework of the invention if the artificial landmark array is introduced into the radiation path of the fluoroscopy apparatus such that it can be removed after imaging. Further navigation (image-assisted surgery) can be performed with the aid of a separately provided navigation reference (reference star).

A system for verifying registration of a fluoroscopy image produced with the aid of a fluoroscopy apparatus includes a navigation system and markings on a radiation source of the fluoroscopy apparatus, wherein the markings are mapped on a fluoroscopy recording as marking point maps. The navigation system is configured to register the fluoroscopy recording onto previously acquired body image data. The system also includes an artificial landmark array that can be located and tracked by the navigation system and which can be introduced into a radiation path of the fluoroscopy apparatus at the time the fluoroscopy recording is produced, and a storage device detects and stores a spatial position of the landmark array at the time the fluoroscopy recording is produced by the navigation system. An output unit of the navigation system can be used for checking a correspondence between an image shadow of the artificial landmark array on the fluoroscopy recording and a position of said landmark array as reproduced in the navigation system.

The storage device can be a part of a computer unit of the navigation system. This is useful, for example, because the navigation system itself will also locate and/or track the position of the landmark array with the aid of a tracking system. In this respect, it may be realized that in accordance with a preferred embodiment of the invention, the artificial landmark array can comprise reference markers that are arranged on a holding structure. The artificial landmark array can be positionally determined and tracked by the tracking and/or camera unit of the navigation system, wherein the landmark array can be pre-calibrated in the navigation system and/or known in terms of its geometry.

The holding structure preferably includes material that can be mapped by x-ray radiation, in particular a material that is semi-permeable or impermeable to x-ray radiation. In a preferred embodiment, the holding structure can be formed in the shape of a cross, with reference markers on outer ends of the structure.

In the following, the invention is explained in more detail on the basis of an exemplary embodiment. The invention can include any of the features described herein, individually or in any combination, and the single enclosed figure, to which reference is now made, schematically shows a system in accordance with the invention.

The invention also relates to a program which, when running on a computer or is loaded onto a computer, causes the computer to perform a method as cited above, and to a computer program storage medium which comprises such a program.

DETAILED DESCRIPTION

Figure 1:
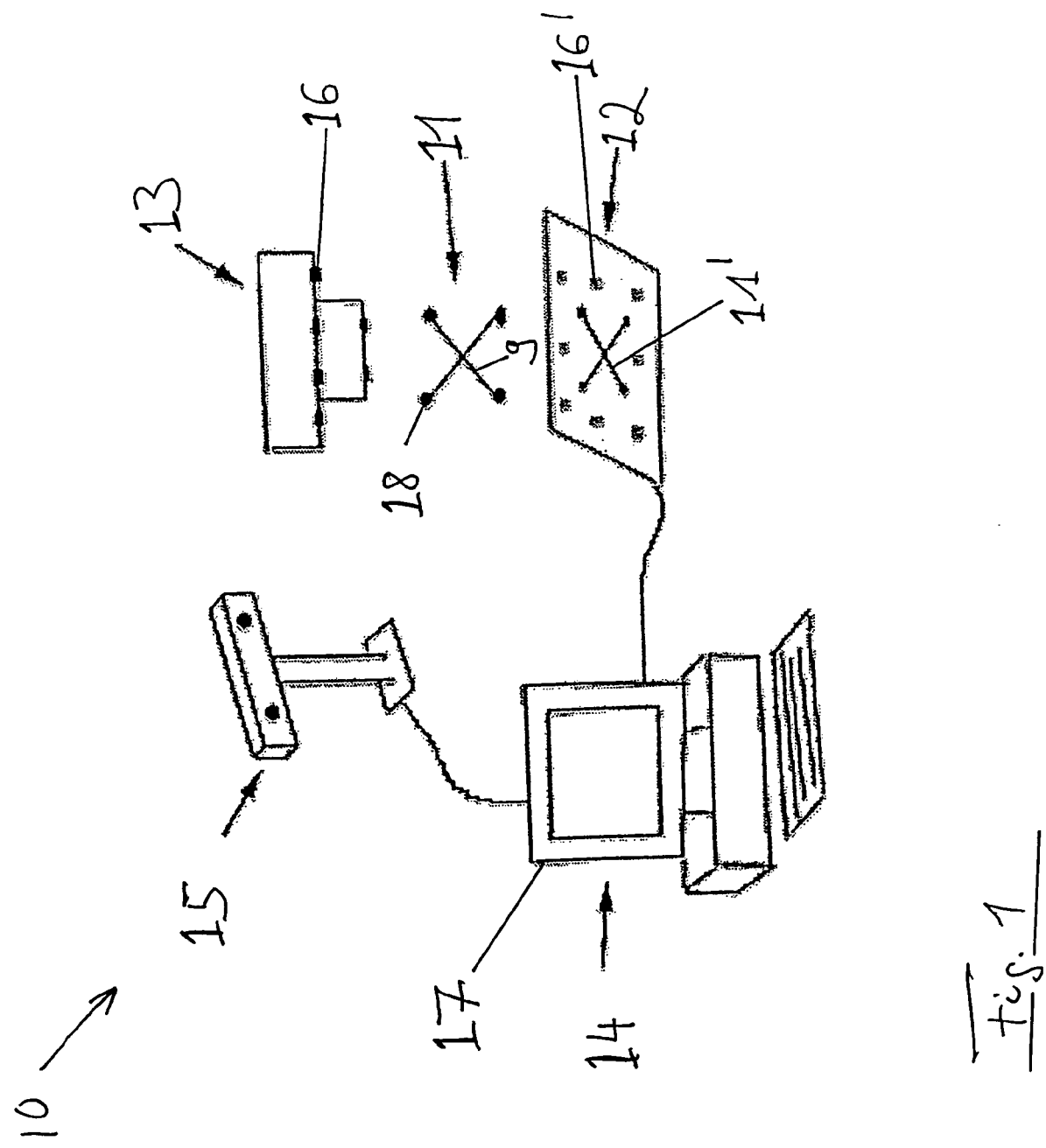
FIG. 1 is a schematic representation of a system for fluoroscopy image verification in accordance with the invention.

FIG. 1 schematically shows a surgical navigation system 10 that includes a computer unit 14, cameras and/or tracking unit 15 and a screen output 17. The navigation system 10 monitors a fluoroscopy device, of which only an attachment 13 is shown in FIG. 1. The attachment 13 is connected to a radiation source of the fluoroscopy apparatus (not shown). The attachment 13 includes markings 16 which, at the time a fluoroscopy recording 12 is produced, are mapped on a fluoroscopy recording 12 as markings 16'. The fluoroscopy recording 12 can be initially registered in the navigation system 10, at least in principle, using an array of different markings 16, also on different planes, pre-calibrated and known in the navigation system, e.g., the image content of the fluoroscopy recording can be spatially correlated with data provided to the navigation system 10. To this end, the spatial position of the fluoroscopy apparatus (not shown) is advantageously determined in the navigation system when the recording is triggered.

FIG. 1 also shows an artificial landmark array 11, which lies in a radiation path between the attachment 13 and the recording 12. The array 11 includes a cruciform holding structure 19, and markers or reference markers 18 are attached to the structure 19. The markers or reference markers 18 can be positionally determined and tracked by the navigation system 10, in particular by the cameras and/or tracking unit 15.

In FIG. 1, the artificial landmark array 11 is mapped as 11' on the fluoroscopy recording 12. The arrangement of reference markers 18 on the landmark array 11 can be clearly recognized by the stereotactic surgical system or navigation system 10. The landmark array 11 represents a clearly identifiably arrangement, the geometry of which can be stored in the navigation system 10.

As indicated above, a spatial relationship between the fluoroscopy recording 12 and the attachment 13 (and therefore the fluoroscopy apparatus) can be determined by the markings 16. This spatial relationship can be used to virtually display the artificial landmark array 11 on the screen output 17.

In order to then verify the accuracy of the spatial relationship between the recording 12 and the attachment 13, the landmark array 11 can be mapped on the recording 12 and a virtual representation of the landmark array 11 can be superimposed onto the map of the array 11 on recording 12. The virtual representation of the landmark array can be superimposed by the navigation system 10 and displayed via the screen output 17. A comparison of the two representations allows the accuracy to be checked, e.g., if the map of the array 11 corresponds to its virtual image from the navigation system 10, then the recording is sufficiently accurate. If this is not the case, then the recording should be repeated.

In addition, a movement by the landmark array 11 with respect to the attachment 13 after the image has been produced will not impair verification, since the spatial position of the landmark array 11 at the time the image was produced is detected by the navigation system 10 (via the reference markers 18, which are tracked by the cameras and/or tracking unit 15) and stored. In this way, the landmark array 11 does not necessarily need to be in the same position for image acquisition and image verification, but can be removed after verification. Further navigation (image-assisted surgery) can be performed with the aid of a separately provided navigation reference (reference star).

Figure 2:
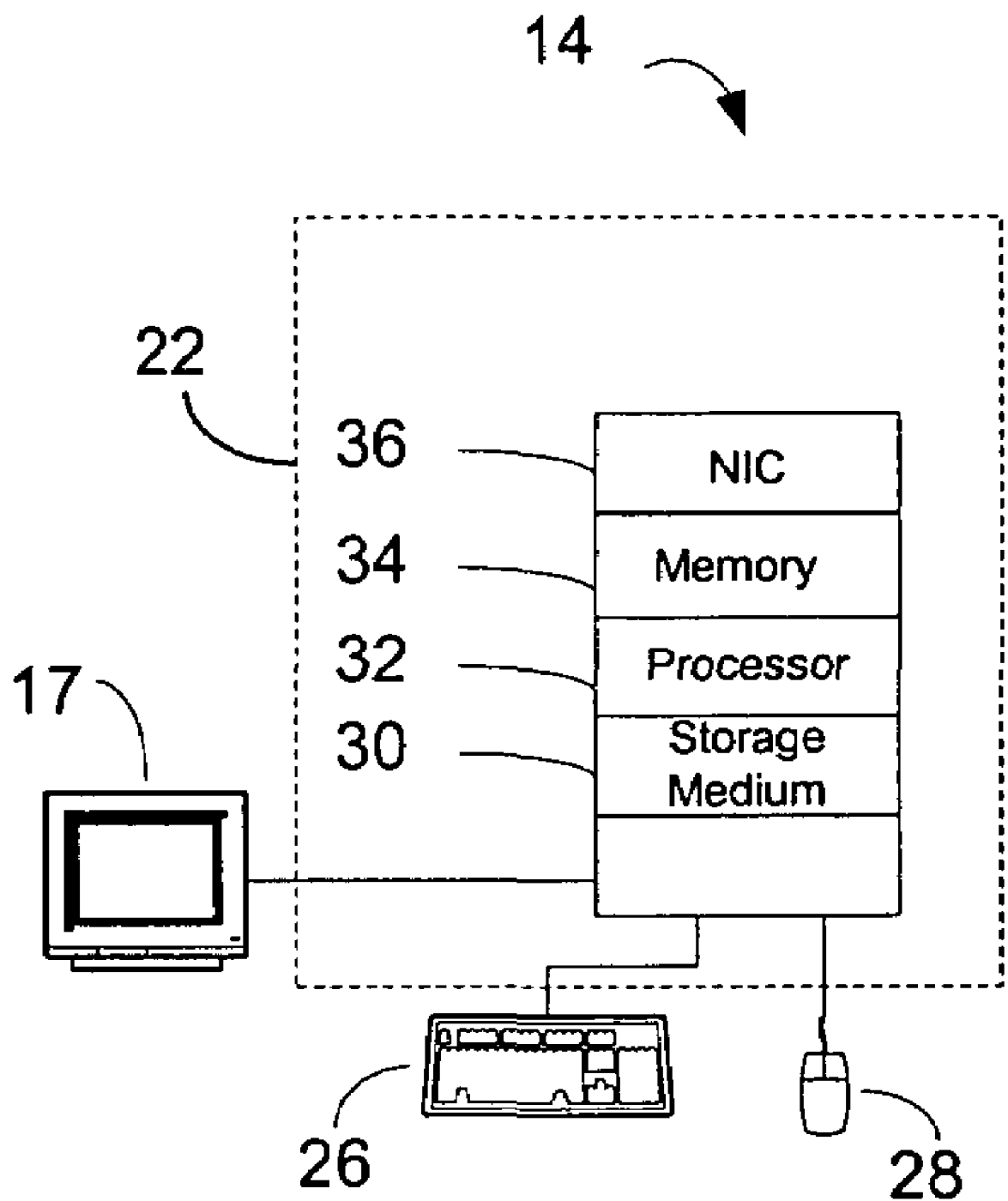
FIG. 2 is a block diagram of a computer system that can be used to implement the method of the present invention.

Moving to FIG. 2, a computer unit 14 for executing a computer program in accordance with the present invention is illustrated. The computer unit 14 can be communicatively coupled to the cameras 15 to receive positional data therefrom, and to display three-dimensional positional data. The computer unit 14 includes a computer 22 for processing data, and a display 17, such as a CRT, LCD, or the like, for viewing system information. A keyboard 26 and pointing device 28 may be used for data entry, data display, screen navigation, etc. The keyboard 26 and pointing device 28 may be separate from the computer 22 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 26 and pointing device 28. A touch screen is well known by those skilled in the art and will not be described in detail herein. Briefly, a touch screen implements a thin transparent membrane over the viewing area of the display 17. Touching the viewing area sends a signal to the computer 22 indicative of the location touched on the screen. The computer 22 may equate the signal in a manner equivalent to a pointing device and act accordingly. For example, an object on the display 17 may be designated in software as having a particular function (e.g., view a different screen). Touching the object may have the same effect as directing the pointing device 28 over the object and selecting the object with the pointing device, e.g., by clicking a mouse. Touch screens may be beneficial when the available space for a keyboard 26 and/or a pointing device 28 is limited.

Included in the computer 22 is a storage medium 30 for storing information, such as application data, screen information, programs, etc. The storage medium 30 may be a hard drive, for example. A processor 32, such as an AMD Athlon 64™ processor or an Intel Pentium IV® processor, combined with a memory 34 and the storage medium 30 execute programs to perform various functions, such as data entry, numerical calculations, screen display, system setup, etc. A network interface card (NIC) 36 allows the computer 22 to communicate with devices external to the computer unit 14.

The actual code for performing the functions described herein can be easily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for verifying the registration of a fluoroscopy image, comprising the steps of:
   introducing an artificial landmark array into a radiation path of a fluoroscopy apparatus, the landmark array being trackable by a computer assisted, medical navigation system;
   producing a fluoroscopy recording with the aid of the fluoroscopy apparatus;
   detecting and storing a spatial position of the artificial landmark array at the time the fluoroscopy recording is produced;
   registering the fluoroscopy recording onto previously acquired body image data of the navigation system using marking points mapped on the fluoroscopy recording, wherein the marking points are maps of markings on the radiation source; and
   checking a correspondence between an image shadow of the artificial landmark array on the fluoroscopy recording and a position of the landmark array at the time the recording was produced.

2. The method as set forth in claim 1, further comprising the step of
   requesting or prompting for a new fluoroscopy recording to be produced if an insufficient correspondence is established.

3. The method as set forth in claim 1, further comprising the step of removing the artificial landmark array.

4. The method as set forth in claim 1, wherein the step of checking the correspondence includes using a position of the landmark array as reproduced in the navigation system.

5. The method as set forth in claim 1, wherein the step of checking the correspondence includes using an output unit of the navigation system.

6. A computer readable medium comprising computer executable instructions adapted to perform the method in accordance with claim 1.

7. The method according to claim 1, wherein introducing the artificial landmark array includes introducing an artificial landmark array configured to emit or reflect light that is trackable by the medical navigation system.

8. A system for verifying registration of a fluoroscopy image produced with the aid of a fluoroscopy apparatus, comprising:
   markings on a radiation source of the fluoroscopy apparatus, wherein the markings are mapped on a fluoroscopy recording as marking point maps;
   a computer-assisted, medical navigation system configured to register the fluoroscopy recording onto previously acquired body image data:
   an artificial landmark array that can be located and tracked by the navigation system and which can be introduced into a radiation path of the fluoroscopy apparatus at the time the fluoroscopy recording is produced;
   a storage device which detects and stores a spatial position of the landmark array at the time the fluoroscopy recording is produced by the navigation system; and
   an output unit of the navigation system for checking a correspondence between an image shadow of the artificial landmark array on the fluoroscopy recording and a position of said landmark array as reproduced in the navigation system.

9. The system as set forth in claim 8, wherein the storage device is a part of a computer unit of the navigation system.

10. The system as set forth in claim 8, wherein the artificial landmark array comprises reference markers that are arranged on a holding structure, wherein the reference markers can be positionally determined and tracked by a tracking unit of the navigation system.

11. The system as set forth in claim 10, wherein the landmark array is pre-calibrated in the navigation system and/or known in terms of its geometry.

12. The device system as set forth in claim 10, wherein the holding structure is formed in a shape of a cross and the reference markers are on outer ends of the holding structure.

13. The system as set forth in claim 8, wherein the holding structure includes a material that can be mapped by x-ray radiation.

14. The system as set forth in claim 13, where the material is semi-permeable or impermeable to x-ray radiation.

15. The system according to claim 8, wherein said artificial landmark array is configured to emit or reflect light that is trackable by the medical navigation system.

16. The System according to claim 8, wherein the medical navigation system comprises an optical tracking unit configured to optically track the artificial landmark array.

17. A computer readable medium comprising computer executable instructions adapted to verify the registration of a fluoroscopy image, wherein an artificial landmark array is introduced into a radiation path of a fluoroscopy apparatus, the landmark array being trackable by a computer assisted, medical navigation system, comprising:
   code configured to direct the production of a fluoroscopy recording with the aid of the fluoroscopy apparatus;
   code configured to detect and store a spatial position of the artificial landmark array at the time the fluoroscopy recording is produced;
   code configured to register the fluoroscopy recording onto previously acquired body image data of the navigation system using marking points mapped on the fluoroscopy recording, wherein the marking points are maps of markings on the radiation source; and
   code configured to check a correspondence between an image shadow of the artificial landmark array on the fluoroscopy recording and a position of the landmark array at the time the recording was produced.

18. A system for verifying the registration of a fluoroscopy image, wherein an artificial landmark array is introduced into a radiation path of a fluoroscopy apparatus, the landmark array being trackable by a computer assisted, medical navigation system, comprising:
- a processor circuit having a processor and a memory;
- a registration sub-system stored in the memory and executable by the processor, the visualization system comprising:
- logic that directs the production of a fluoroscopy recording with the aid of the fluoroscopy apparatus;
- logic that detects and stores a spatial position of the artificial landmark array at the time the fluoroscopy recording is produced;
- logic that registers the fluoroscopy recording onto previously acquired body image data of the navigation system using marking points mapped on the fluoroscopy recording, wherein the marking points are maps of markings on the radiation source; and
- logic that checks a correspondence between an image shadow of the artificial landmark array on the fluoroscopy recording and a position of the landmark array at the time the recording was produced.

* * * * *